United States Patent [19]

Torelli et al.

[11] 4,376,734

[45] Mar. 15, 1983

[54] PROCESS FOR 3-AMINO-STEROID PREPARATION

[75] Inventors: Vesperto Torelli, Maisons Alfort; Lucien Nedelec, Le Raincy, both of France

[73] Assignee: Roussel Uclaf, Paris, France

[21] Appl. No.: 319,912

[22] Filed: Nov. 10, 1981

[30] Foreign Application Priority Data

Nov. 21, 1980 [FR] France ................... 80 24748

[51] Int. Cl.³ ........................ C07J 5/00; C07J 7/00
[52] U.S. Cl. ........................ 260/397.3; 260/397.5; 260/349
[58] Field of Search ................ 260/397.3, 397.5

[56] References Cited

U.S. PATENT DOCUMENTS 3,445,461  5/1969  Borrevang et al. .......... 260/239.5
3,862,196  1/1975  Hewett et al. ............. 260/397.4

*Primary Examiner*—Elbert L. Roberts
*Attorney, Agent, or Firm*—Hammond & Littell, Weissenberger and Muserlian

[57] ABSTRACT

A novel process for the preparation of 3-amino-steroids of the formula

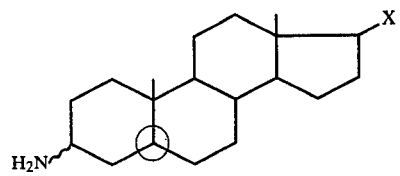

wherein X is selected from the group consisting of

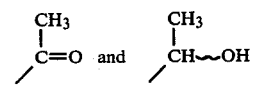

and the wavy lines indicate that the substituents may be in the α- or β-position and their non-toxic, pharmaceutically acceptable acid addition salts in good yields and novel intermediates.

7 Claims, No Drawings

PROCESS FOR 3-AMINO-STEROID PREPARATION

STATE OF THE ART

Bansi Lal et al [Tetrahedron Letters, No. 23 (1977), p. 1977–1980] describes the stereospecific synthesis of azides from alcohols using the same reactants as the presently claimed process but the steroids are different and the transformation of the azides into amines is not taught.

OBJECTS OF THE INVENTION

It is an object of the invention to provide a novel process for the preparation of the 3-amino-steroids of formula I and their acid addition salts.

It is another object of the invention to provide novel intermediate products.

These and other objects and advantages of the invention will become obvious from the following detailed description.

THE INVENTION

The novel process of the invention for the preparation of 3-amino-steroids of the formula

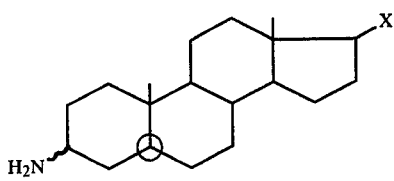

wherein X is selected from the group consisting of

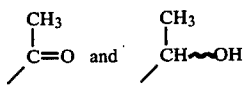

and the wavy lines indicate that the substituents may be in the α- or β-position and their non-toxic, pharmaceutically acceptable acid addition salts comprises transforming a compound of the formula

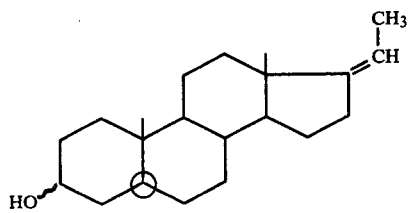

wherein the wavy lines has the above definition into the corresponding azide of the formula

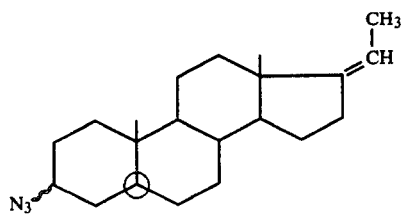

wherein the 3-azide group is inverted to the position of 3-hydroxyl group of formula II, reducing the latter to the 3-amino compound of the formula with the same configuration

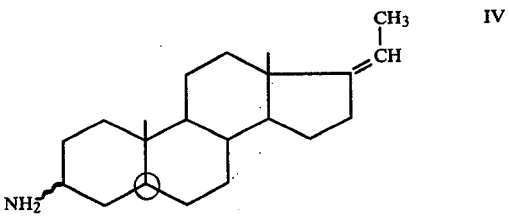

subjecting the latter to hydration to obtain the corresponding compound of formula I wherein X is

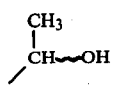

which may be isolated and salified if desired, and optionally reacting the latter with an oxidation agent to obtain the corresponding compound of formula I wherein X is

which may be isolated and salified, if desired.

The transformation of the alcohol of formula II into the azide of formula III may be effected by the classical method of forming the tosylate of the alcohol and reacting the latter with sodium azide, for example, to form the 3-azido compound. In a preferred mode of the process, the transformation is effected with diphenyl azidophosphate in the presence of ethyl azidocarboxylate and triphenylphosphine, preferably with an excess of the said 3 reactants, most preferably 2 moles of each per mole of alcohol. The reaction may be effected at room temperature but is preferably effected by cooling to about 5° C. The reaction is effected in an organic solvent such as benzene or tetrahydrofuran or mixtures thereof.

The transformation is stereoselective with the 3α-alcohol leading to the 3β-azido compound and the 3β-alcohol leading to the 3α-azido compound. Also operative are mixtures of the 3α- and 3β-alcohols. The stereochemical configuration of the azide is kept through the rest of the process whereby the 3-amino-steroid of formula I has the inverse configuration of the starting 3-alcohol of formula II.

The reduction of the azide of formula III is preferably effected with an alkali metal hydride such as diisobutyl aluminum hydride, sodium borohydride, an alcoxy aluminium lithium hydride-and especially with lithium aluminum hydride in an inert solvent such as ether, dioxane, benzene, toluene, chloroform or especially tetrahydrofuran. The reduction is preferably effected at 10° to 30° C., especially about 20° C. Equally useful is a catalytic reduction, preferably in the presence of palladium or nickel.

The hydration of the amine of formula IV is preferably effected with an alkylborane or diborane followed by an alkaline oxidation. Diborane, preferably formed in situ, is preferably used when the compound of formula I is to have the 20-hydroxyl in the α-or (S) configuration. In this case, an alkali metal borohydride such as sodium or potassium borohydride is reacted with boron trifluoride.

The diborane is used in a complexed form such as a complex with $BH_3$, $S(CH_3)_2$ when the compound of formula I is to have the 20-hydroxyl in the β-or (R) configuration and the α- or (S) configuration is essentially equal proportions. The alkaline oxidation is preferably the classical reaction with hydrogen peroxide in the presence of sodium hydroxide or potassium hydroxide in an organic solvent as discussed above.

The oxidation of the 20-hydroxyl steroids of formula I may be effected, for example, by the Oppenhauer reaction with an excess of a ketone in the presence of aluminum alkoxide but other oxidation agents such as chromic acid or its alkali metal dichromate derivatives may be used.

The compounds of formula I have a basic character and the acid addition salts thereof may be prepared by reaction with about stoichiometric proportions of a non-toxic, pharmaceutically acceptable acid such as inorganic acids like hydrochloric acid, hydrobromic acid, sulfuric acid, phosphoric acid or nitric acid or organic acids such as acetic acid, formic acid, citric acid, oxalic acid, etc. The salts may be prepared without isolation of the free base.

If desired, the products of each step of the process of the invention may be used in the form of its individual isomers or as mixtures. The mixtures of isomers may be separated by claasical methods such as crystallization or chromatography.

The products of formula I are known compounds and include funtumine or 3α-amino-5α-pregnane-20-one which is extracted from Funtumia latifolia Stapf, leaves of Apocynacees as well as funtimidine or 3α-amino-5α-pregnane-20α-ol prepared by reduction of funtumine. The process of the invention has the particular advantage of leading to 3-amino derivatives specifically in the α- or β-position in very good yields.

The novel intermediates of the invention are the compounds of formulae III and IV.

The starting alcohol of formula II may be prepared by known procedure. For example, the 3α-alcohol may be prepared by the Wittig reaction using the procedure of Krubiner et al [J. Org. Chem., Vol. 31 (1966), p. 24] beginning with the ketone of the formula

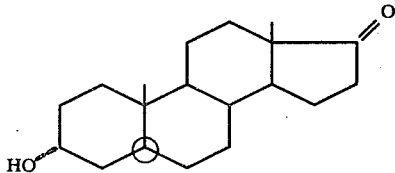

which is described in French Pat. No. 1,058,455.

In the following example there are described several preferred embodiments to illustrate the invention. However, it should be understood that the invention is not intended to be limited to the specific embodiments.

EXAMPLE (20S) 3α-amino-5α-pregnane-20-ol

STEP A: (Z) 3α-azido-5α-$\Delta^{17(20)}$-pregnene 1.92 g of ethyl azodicarboxylate and 3.02 g of diphenyl azidophosphate were added with stirring at 5° C. to a solution of 1.66 g of (Z) 5α-$\Delta^{17(20)}$-pregnene-3α-ol [Krubiner et al, J. Org. Chem., Vol. 31 (1966), p. 24], 30 ml of benzene and 5 ml of tetrahydrofuran and then a solution of 2.88 g of triphenylphosphine in 30 ml of benzene was added to the mixture over 20 minutes. The mixture was stirred at 10° C. for 40 minutes and was washed with 2 N hydrochloric acid solution, then with water and was dried and evaporated to dryness. The residue was chromatographed over silica gel and was eluted with heptane and then a 1-1 heptane-ether mixture to obtain 1.67 g of (Z) 3α-azido-5α-$\Delta^{17(20)}$-pregnene which melted at 114° C. after crystallization from methanol.

STEP B: (Z) 3α-amino-(5α)-$\Delta^{17(20)}$-pregnene hydrochloride 14.5 g of the product of Step A were dissolved by stirring in 29 ml of tetrahydrofuran heated to 25°-27° C. and 800 mg of lithium aluminum hydride were added thereto over one hour while keeping the temperature at 35° C. The mixture was stirred for one hour and methanol was added to the mixture to destroy excess hydride. The mixture was filtered and the filter was washed with ethyl acetate. The filtrate was washed with a solution of Seignette salt and then with aqueous saturated sodium chloride solution, was dried and evaporated to dryness to obtain 13.1 g of (Z) 3α-amino-(5α)-$\Delta^{17(20)}$-pregnene in the form of crystals melting at ≈90° C. The said product was dissolved in 150 ml of ethyl acetate and 30 ml of methylene chloride and 27 ml of 1.7 N hydrogen chloride in ethyl acetate were added thereto. The mixture was vacuum filtered and the product was dried under reduced pressure to obtain 13.2 g of (Z) 3α-amino-(5α)-$\Delta^{17(20)}$-pregnene hydrochloride melting at >300° C.

STEP C: (20 S) 3α-amino-5α-pregnane-20-ol

A solution of 0.5 ml boron trifluoride-etherate in 2.5 ml of tetrahydrofuran was added dropwise at 5° C. under a nitrogen atmosphere to a suspension of 150 mg of sodium borohydride in 5 ml of tetrahydrofuran and the mixture was stirred at 5° to 10° C. for one hour. A solution of 300 mg of the free base of Step B in 3 ml of tetrahydrofuran was added to the mixture which was stirred at room temperature for 90 minutes and was then cooled to 5° C. 2 ml of 6 N sodium hydroxide solution were slowly added to the mixture which was then stirred at room temperature for 5 minutes. The decanted aqueous phase was extracted with tetrahydrofuran and the combined organic phases were washed with 5 N sodium hydroxide solution. 4 ml of 5 N sodium hydroxide solution and 2 ml of hydrogenperoxide at 110 volumes were added to the organic phase which was then stirred for 45 minutes. The mixture was extracted with ethyl acetate and the organic phase was washed with aqueous 10% sodium thiosulfate solution, with water, was dried and evaporated to dryness under reduced pressure. The dry residue was taken up in 10 ml of methanol and 5 ml of N hydrochloric acid and the mixture was heated at 50° C. for 30 minutes and was poured into an aqueous saturated sodium bicarbonate solution. The mixture was extracted with methylene chloride and the organic phase was washed with water, dried and evaporated to dryness under reduced pressure to obtain 270 mg of (20S) 3α-amino-5α-pregnane-20-ol melting at 180°-182° C.

Various modifications of the products and processes of the invention may be made without departing from the spirit or scope thereof and it should be understood that the invention is intended to be limited only as defined in the appended claims.

What we claim is:

1. A process for the preparation of 3-amino-steroids of the formula

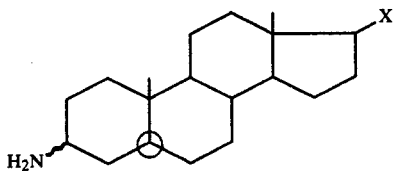

wherein X is selected from the group consisting of

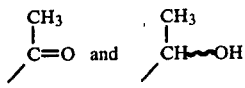

and the wavy lines indicate that the substituents may be in the α- or β-position and their non-toxic, pharmaceutically acceptable acid addition salts comprising transforming a compound of the formula

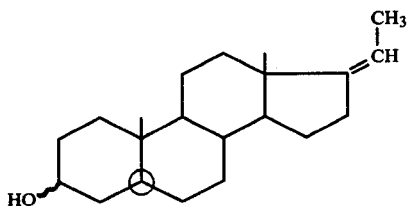

wherein the wavy line has the above definition into the corresponding azide of the formula

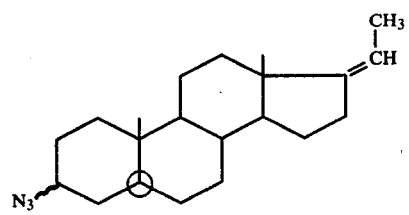

wherein the 3-azide group is inverted to the position of 3-hydroxyl group of formula II, reducing the latter to the 3-amino compound of the formula with the same configuration

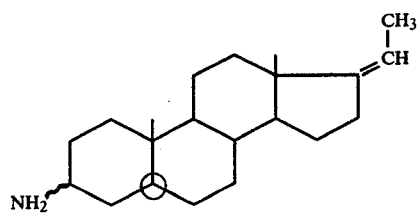

subjecting the latter to hydration to obtain the corresponding compound of formula I wherein X is

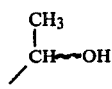

which may be isolated and salified if desired, and optionally reacting the latter with an oxidation agent to obtain the corresponding compound of formula I wherein X is

which may be isolated and salified, if desired.

2. The process of claim 1 wherein the transformation of the alcohol of formula II is effected with diphenyl azidophosphate in the presence of ethyl azidocarboxylate and triphenylphosphine.

3. The process of claim 1 or 2 wherein the azide reduction is effected with lithium aluminum hydride.

4. The process of claim 3 wherein the reduction is effected at 10° to 30° C.

5. The process of claim 1 or 2 wherein the hydration of the amine of formula IV is effected with an alkyl borane followed by an alkaline oxidation.

6. The process of claim 1 or 2 wherein the hydration of the amine of formula IV is effected with diborane followed by an alkaline oxidation.

7. The process of claim 6 wherein the diborane is prepared extemporaneously at the time of use.

* * * * *